United States Patent
Nakatani et al.

(10) Patent No.: US 9,932,239 B2
(45) Date of Patent: Apr. 3, 2018

(54) SHEET-LIKE FIBER STRUCTURE, AND BATTERY, HEAT INSULATION MATERIAL, WATERPROOF SHEET, SCAFFOLD FOR CELL CULTURE, AND HOLDING MATERIAL EACH USING THE SHEET-LIKE FIBER STRUCTURE

(75) Inventors: Masaya Nakatani, Hyogo (JP);
Makoto Takahashi, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 370 days.

(21) Appl. No.: 13/620,493

(22) Filed: Sep. 14, 2012

(65) Prior Publication Data

US 2013/0017450 A1  Jan. 17, 2013

(30) Foreign Application Priority Data

Apr. 27, 2010  (JP) ................................. 2010-101730

(51) Int. Cl.
*B32B 3/26* (2006.01)
*B32B 5/16* (2006.01)
(Continued)

(52) U.S. Cl.
CPC ............... *C01B 33/12* (2013.01); *B32B 5/26* (2013.01); *B82Y 30/00* (2013.01); *C01B 33/18* (2013.01); *C04B 35/6224* (2013.01); *C12N 5/0068* (2013.01); *D04H 3/002* (2013.01); *D04H 3/105* (2013.01); *D04H 3/14* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 4,720,713 A | 1/1988 | Chang et al. | |
| 5,629,186 A | 5/1997 | Yasukawa et al. | |
| (Continued) | | | |

FOREIGN PATENT DOCUMENTS

| | | |
|---|---|---|
| CN | 101489656 A | 7/2009 |
| EP | 2 172 415 A1 | 4/2010 |
| | (Continued) | |

OTHER PUBLICATIONS

Michielsen et al., "Review of Thermally Point-Bonded Nonwovens: Materials, Processes, Properties," Available Online Dec. 2005, Journal of Applied Polymer Science, vol. 99, 2489-2496.*

(Continued)

*Primary Examiner* — Ula C Ruddock
*Assistant Examiner* — Matthew W Van Oudenaren
(74) *Attorney, Agent, or Firm* — McDermott Will & Emery LLP

(57) ABSTRACT

A sheet-like fiber structure including a plurality of fibers made of amorphous silicon dioxide. The plurality of fibers are intertwined with each other and thus connected to each other, thereby forming void portions. Consequently, the sheet-like fiber structure has not only liquid permeability and voltage resistance but also high heat resistance and chemical resistance. The sheet-like fiber structure is therefore applicable to a separator for preventing a short circuit between electrodes, a scaffold for cell culture, to holding a biomolecule, or the like.

20 Claims, 6 Drawing Sheets

(51) Int. Cl.
| | |
|---|---|
| H01M 2/16 | (2006.01) |
| C01B 33/12 | (2006.01) |
| B32B 5/26 | (2006.01) |
| B82Y 30/00 | (2011.01) |
| C01B 33/18 | (2006.01) |
| C04B 35/622 | (2006.01) |
| D04H 3/002 | (2012.01) |
| D04H 3/105 | (2012.01) |
| D04H 3/14 | (2012.01) |
| C12N 5/00 | (2006.01) |
| H01M 2/14 | (2006.01) |
| H01M 2/18 | (2006.01) |

(52) U.S. Cl.
CPC ...... C01P 2004/03 (2013.01); C01P 2004/17 (2013.01); C04B 2235/526 (2013.01); C04B 2235/5232 (2013.01); C04B 2235/5264 (2013.01); C04B 2235/5268 (2013.01); C12N 2533/12 (2013.01); H01M 2/14 (2013.01); H01M 2/162 (2013.01); H01M 2/1606 (2013.01); H01M 2/1613 (2013.01); H01M 2/1626 (2013.01); H01M 2/1633 (2013.01); H01M 2/18 (2013.01); Y10T 428/249921 (2015.04); Y10T 428/249964 (2015.04)

(56) References Cited

U.S. PATENT DOCUMENTS

| | | | |
|---|---|---|---|
| 6,080,471 A * | 6/2000 | Shigematsu | D04H 1/42 162/157.5 |
| 6,296,969 B1 | 10/2001 | Yano et al. | |
| 6,485,856 B1 * | 11/2002 | Brown et al. | 429/492 |
| 2003/0059670 A1 * | 3/2003 | Bechtold et al. | 429/94 |
| 2004/0058102 A1 * | 3/2004 | Baychar | 428/34.1 |
| 2004/0197898 A1 | 10/2004 | Nakatani et al. | |
| 2004/0266000 A1 * | 12/2004 | Offermann et al. | 435/398 |
| 2004/0266299 A1 | 12/2004 | Fongalland et al. | |
| 2005/0112756 A1 | 5/2005 | Nakatani et al. | |
| 2005/0214740 A1 | 9/2005 | Ushio et al. | |
| 2005/0221469 A1 | 10/2005 | Nakatani et al. | |
| 2006/0154128 A1 * | 7/2006 | Kim | C08J 5/2275 429/483 |
| 2007/0105183 A1 | 5/2007 | Nakatani et al. | |
| 2007/0264577 A1 | 11/2007 | Katayama et al. | |
| 2008/0237039 A1 | 10/2008 | Nakatani et al. | |
| 2008/0257726 A1 | 10/2008 | Nakatani et al. | |
| 2008/0257727 A1 | 10/2008 | Nakatani et al. | |
| 2009/0035846 A1 | 2/2009 | Nakatani et al. | |
| 2009/0047731 A1 | 2/2009 | Nakatani et al. | |
| 2009/0067119 A1 | 3/2009 | Katayama et al. | |
| 2009/0152110 A1 | 6/2009 | Hiraoka et al. | |
| 2009/0178922 A1 | 7/2009 | Nakatani et al. | |
| 2009/0197333 A1 | 8/2009 | Saito et al. | |
| 2009/0239033 A1 | 9/2009 | Nakatani et al. | |
| 2009/0301304 A1 | 12/2009 | Bass et al. | |
| 2010/0019756 A1 | 1/2010 | Hiraoka et al. | |
| 2010/0019782 A1 | 1/2010 | Watanabe et al. | |
| 2010/0147682 A1 | 6/2010 | Nakatani et al. | |
| 2010/0219488 A1 * | 9/2010 | Nakatani | B81C 1/00206 257/414 |
| 2010/0270148 A1 | 10/2010 | Nakatani et al. | |
| 2013/0040094 A1 | 2/2013 | Nakatani et al. | |

FOREIGN PATENT DOCUMENTS

| | | |
|---|---|---|
| JP | 62-257842 A | 11/1987 |
| JP | 62-257842 A | 11/1987 |
| JP | 63-196280 A | 8/1988 |
| JP | 11-209185 | 8/1999 |
| JP | 2000-000401 | 1/2000 |
| JP | 2001-032162 A | 2/2001 |
| JP | 2002-527881 A | 8/2002 |
| JP | 2007-132425 A | 5/2007 |
| JP | 2008-117950 A | 5/2008 |
| JP | 2008-243825 A | 10/2008 |
| WO | 2000/023510 | 4/2000 |
| WO | 2009/034697 A1 | 3/2009 |
| WO | WO-2009/034697 A1 | 3/2009 |
| WO | WO2009034697 * | 3/2009 |
| WO | WO2009117114 * | 9/2009 |

OTHER PUBLICATIONS

English translation Search Report Chinese Patent Application No. 201180021010.8 dated Jul. 18, 2014.
International Search Report issued in PCT/JP2011/002272 dated Jul. 12, 2011.
The Extended European Search Report dated Oct. 31, 2016 for the related European Patent Application No. 11774590.1.
Siddharth V. Patwardhan et al: "Formation of fiber-like amorphous silica structures by externally applied shear", Journal of Inorganic and Organometallic Polymers, vol. 11, No. 2, Jun. 1, 2001 (Jun. 1, 2001), pp. 117-121, XP055310174.

* cited by examiner

SHEET-LIKE FIBER STRUCTURE, AND BATTERY, HEAT INSULATION MATERIAL, WATERPROOF SHEET, SCAFFOLD FOR CELL CULTURE, AND HOLDING MATERIAL EACH USING THE SHEET-LIKE FIBER STRUCTURE

This application is a continuation-in-part application of International Application PCT/JP2011/002272, filed Apr. 19, 2011, claiming the foreign priority of Japanese Patent Application No. 2010-101730, filed Apr. 27, 2010, the contents of which are incorporated herein by reference.

TECHNICAL FIELD

The present invention relates to a sheet-like fiber structure used for various electronic devices that require a heat-insulating property, heat resistance, and voltage resistance, for culture dish materials in cell culture, for holding a biomolecule, and the like, as well as a battery, a heat insulation material, a waterproof sheet and a scaffold for cell culture, each using the sheet-like fiber structure.

BACKGROUND ART

Conventionally, a sheet-like fiber structure including inorganic substances such as silicon dioxide and glass, and organic materials such as cellulose, polypropylene and polyamide is used as a heat insulation material or a voltage resistance material.

Electrolytic capacitors, storage batteries, and the like, have a voltage resistance material called a separator, which is disposed together with an electrolytic solution between a positive electrode and a negative electrode. While the separator prevents a short circuit between the electrodes, it allows ions or electrons existing in the electrolytic solution to permeate thereinto.

Recently, however, storage batteries and the like have had a higher capacity and a higher power. Accordingly, it is necessary to reduce a distance between electrodes as much as possible and, to secure voltage resistance characteristics and liquid permeability. Furthermore, when a short circuit accidentally occurs because foreign matters exist between the electrodes, heat is generated in the vicinity of a place in which the short circuit occurs. As a result, a separator may be damaged due to a high temperature.

Furthermore, a composite of a polymer material and an inorganic material is used as a culture dish material to be used during cell culture. The composite is formed by filling or laminating the inorganic material such as silicon dioxide to the polymer material such as an olefin polymer and a polyester resin. Herein, it is preferable to use polymer materials, which are formed in a form of a porous shape, a tubular shape, a hollow fiber shape, and the like.

In a structure to be used as a culture dish during cell culture, a scaffold to which cells are attached may be disposed such that the cell culture is carried out efficiently. The scaffold supplies sufficient nutrient and, if necessary, carbon dioxide gas, air, and the like, to a group of cells that are being cultured.

The scaffold to be used for a cell culture dish is required to have liquid permeability and air permeability because it needs to supply sufficient nutrient and gas to a group of cells. Furthermore, when the scaffold is subjected to surface treatment, heat treatment or chemical treatment is required to be carried out. Therefore, the scaffold is required to have heat resistance and chemical resistance.

Note here that as prior art literatures regarding the invention, the following Patent Literatures are known.

CITATION LIST

Patent Literature

PTL 1: Japanese Patent Application Unexamined Publication No. 2008-243825
PTL 2: Japanese Patent Application Unexamined Publication No. 2008-117950
PTL 3: Japanese Patent Application Unexamined Publication No. S63-196280

SUMMARY OF THE INVENTION

A sheet-like fiber structure of the present invention includes a plurality of fibers made of amorphous silicon dioxide. The plurality of fibers are intertwined with each other and thus connected to each other, thereby forming void portions.

Since the sheet-like fiber structure of the present invention has an amorphous structure, it has higher flexibility as compared with crystal fiber. Consequently, even when the sheet-like fiber structure is folded or subjected to a pressure when it is used as a separator for a storage battery or an electrolytic capacitor, a sheet structure is not easily damaged.

Furthermore, the sheet-like fiber structure has heat resistance against a temperature as high as not lower than 1000° C. Therefore, even when heat is generated in the vicinity of the sheet, the sheet structure is not damaged. Consequently, the sheet-like fiber structure can be used for a storage battery having a high capacity and a large current. Furthermore, when the sheet-like fiber structure is used for a scaffold to be used for a cell culture dish, the sheet structure is not easily damaged even under heat treatment.

Furthermore, amorphous silicon dioxide is a material having a high alkali resistance property and a high acid resistance property. Therefore, when the sheet-like fiber structure is used as a separator, even if it is soaked in, for example, an electrolytic solution, it is less deteriorated. Furthermore, when the sheet-like fiber structure is used as a scaffold, even if it is surface-treated by chemical treatment, the sheet structure is not damaged.

Furthermore, since the fiber has a diameter that is as thin as not less than 0.01 µm and not more than 1 µm, when the sheet-like fiber structure is used as a separator, percentage of voids and liquid permeability of the sheet become higher. Thus, the separator has smaller thickness, higher liquid permeability and higher voltage resistance as compared with a conventional separator. Furthermore, when the sheet-like fiber structure is used as a scaffold, since an area that is brought into contact with the cell membrane is an extremely small part as a nano-structure, the percentage of voids and the liquid permeability of the sheet become higher. Therefore, it has smaller thickness and higher liquid permeability as compared with a conventional scaffold. As a result, a nutritious substance from a culture solution that passes through the inside of the sheet-like fiber structure can be sufficiently supplied.

DETAILED DESCRIPTION OF THE PREFERRED EMBODIMENT

Hereinafter, exemplary embodiments of the present invention are described with reference to drawings. The present invention is not limited to these exemplary embodiments.

First Exemplary Embodiment

Figure 1A:
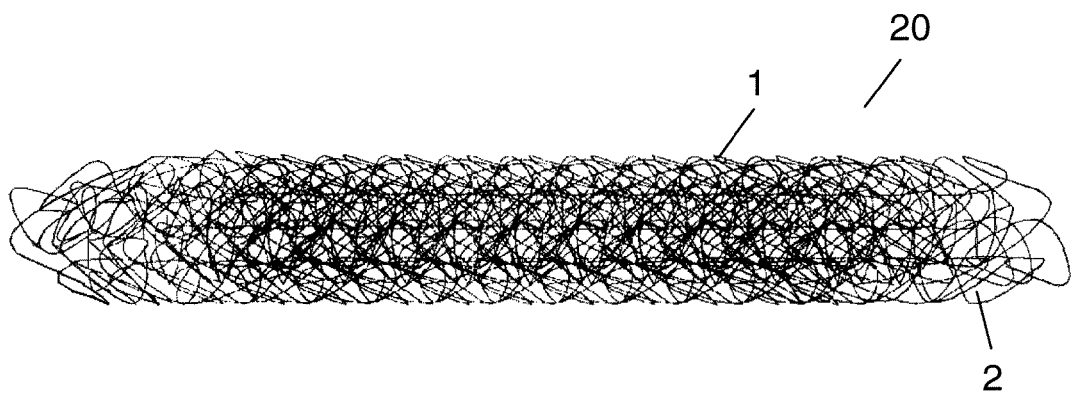
FIG. 1A is a side view of a sheet-like fiber structure in accordance with a first exemplary embodiment of the present invention.
Figure 1B:
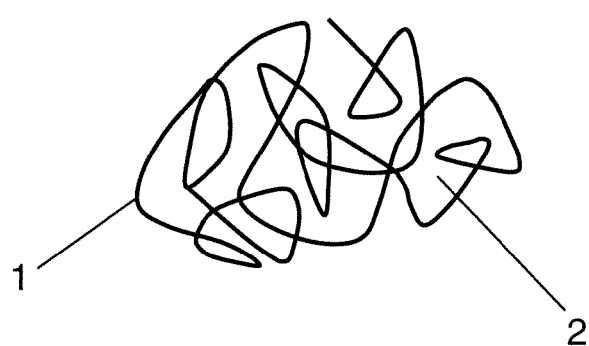
FIG. 1B is an enlarged view of a principal part of the sheet-like fiber structure in accordance with the first exemplary embodiment of the present invention.
Figure 2:
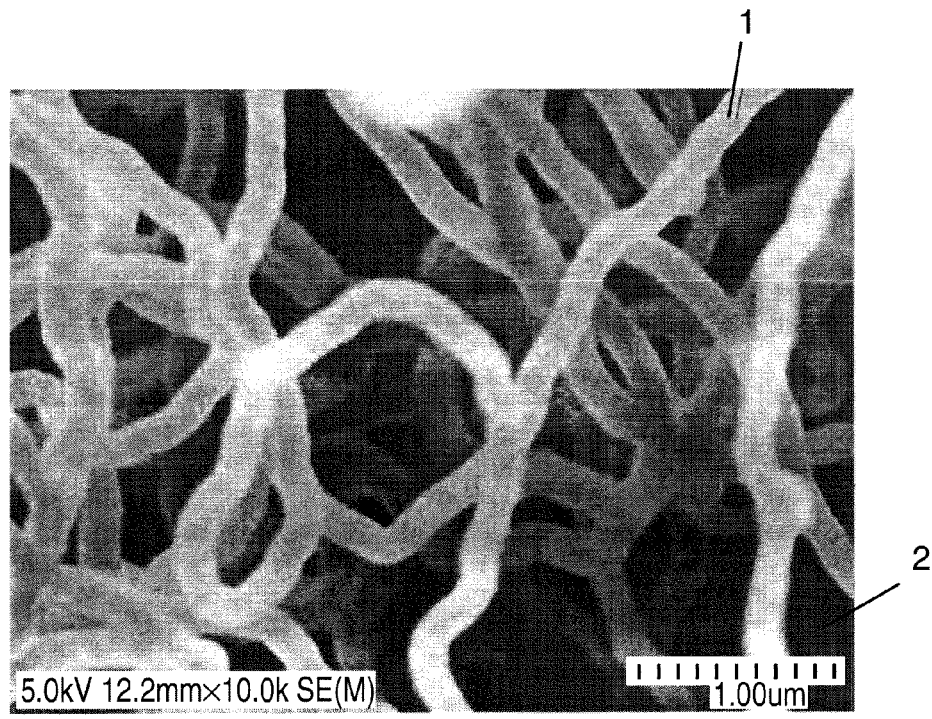
FIG. 2 is a view showing a SEM image of the sheet-like fiber structure in accordance with the first exemplary embodiment of the present invention.
Figure 3:
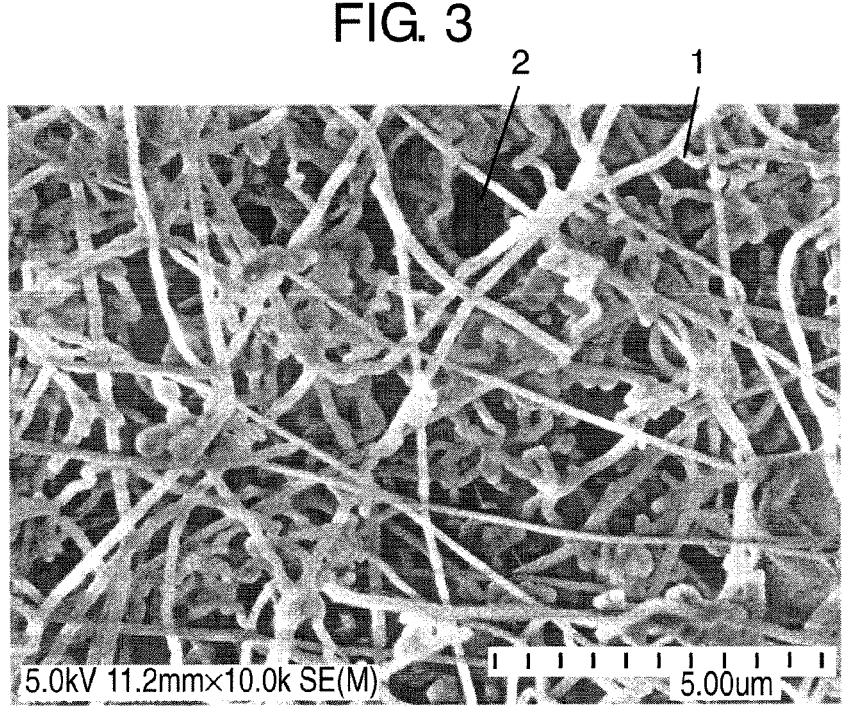
FIG. 3 is a view showing a SEM image of the sheet-like fiber structure in accordance with the first exemplary embodiment of the present invention.
Figure 4:
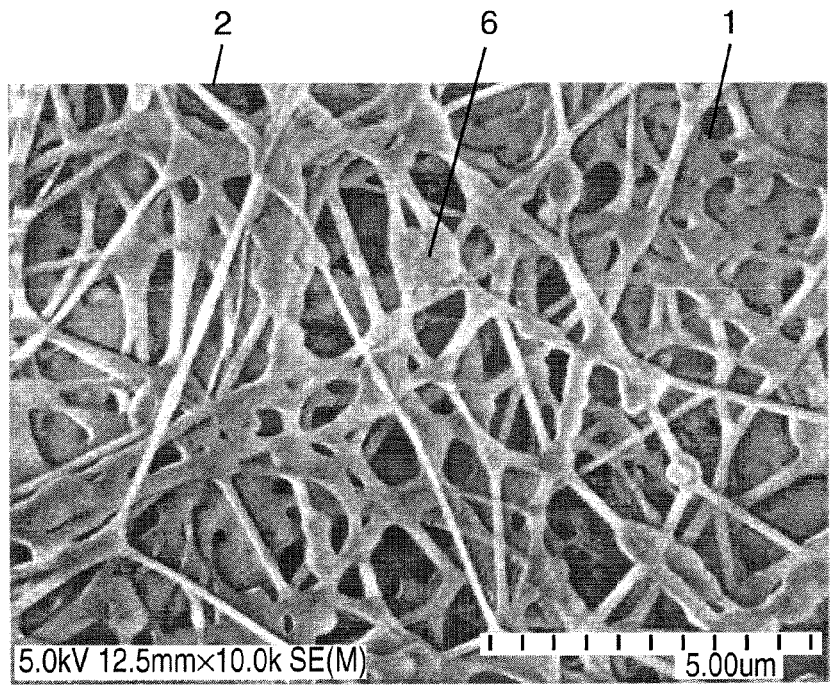
FIG. 4 is a view showing a SEM image of a connection portion of the sheet-like fiber structure in accordance with the first exemplary embodiment of the present invention.

FIG. 1A is a side view of a sheet-like fiber structure in accordance with a first exemplary embodiment of the present invention. FIG. 1B is an enlarged view of a principal part of the sheet-like fiber structure in accordance with the first exemplary embodiment of the present invention. FIG. 2 is a view showing a SEM image of the sheet-like fiber structure in accordance with the first exemplary embodiment of the present invention. FIG. 3 is a view showing a SEM image of the sheet-like fiber structure in accordance with the first exemplary embodiment of the present invention. FIG. 4 is a view showing a SEM image of a connection portion of the sheet-like fiber structure in accordance with the first exemplary embodiment of the present invention.

As shown in FIGS. 1A to 3, sheet-like fiber structure 20 includes fibers 1 made of amorphous silicon dioxide, which are intertwined with each other and connected to each other, thereby forming void portions 2 through which air and a solution are allowed to pass. Fibers 1 are intertwined with each other and densely aggregated in a state in which they are appropriately curled. Furthermore, as shown in FIG. 4, fibers 1 may be connected to each other by connection portion 6 formed by fibers 1 part of which are melted to each other. Thus, fibers 1 are linked together more strongly. Since connection portions 6 are provided in this way, neighboring fibers 1 support each other. Consequently, fibers 1 become stronger as compared with a case in which connection portions 6 are not provided.

Next, an example of a manufacturing method of sheet-like fiber structure 20 is described.

Firstly, particles or a substrate made of Si as a raw material is prepared. The raw material and a gas containing at least an oxygen atom are mixed with each other, and the mixture is heated at 1000° C. to 1500° C. by using, for example, a heater. The raw material is vaporized when it reaches its vapor pressure temperature. The vaporized raw material is bonded to oxygen contained in the gas to form silicon monoxide (SiO), and then coagulated, which takes oxygen in the atmosphere therein so as to form silicon dioxide ($SiO_2$). Thus, fibers 1 are deposited.

Herein, when a substance as a core is present in the vicinity of SiO, coagulation easily occurs, and fibers 1 are deposited efficiently. Examples of the substance as a core include metal such as Pt, Fe, Co, Ni or Au, and types of metal are not particularly limited. Furthermore, the substance as a core is not necessarily required.

When the pressure at the time of heating is made to be lower than the atmospheric pressure, a vapor pressure temperature of the raw material is reduced and vaporization easily occurs. Therefore, a larger amount of fibers 1 can be formed. When the temperature is increased in a state in which as much oxygen as possible is removed, and the temperature is maintained in a reduced oxygen partial pressure, for example, at $10^{-2}$ Pa to several thousands Pa, in which a small amount of oxygen is added, the productivity of fibers 1 is improved.

The thus deposited fibers 1 are intertwined with each other and overlapped to each other, and thereby sheet-like fiber structure 20 is formed. At this time, a sheet may be formed during a process in which fibers 1 are grown, and a sheet may be formed after fibers 1 are grown and formed. Such a condition is dependent upon the temperature at which fibers 1 are formed.

Furthermore, when heat of about not lower than 1100° C. is applied to sheet-like fiber structure 20, sheet-like fiber structure 20 is thermally melted. The thermally melted $SiO_2$ fibers are bonded together when they have portions that are brought into contact with neighboring fibers during a cooling process, so that as shown in FIG. 4, sheet-like fiber structure 20 including a plurality of connection portions 6 is formed. Since the thus connected sheet-like fiber structure includes void portions 2, a surface area thereof can be kept large. Furthermore, since fibers 1 support each other, the structure becomes stronger as compared with a case in which connection portion 6 is not provided.

Note here that connection portion 6 may be formed in a process in which fibers 1 are grown. The formation of connection portion 6 depends on the temperature at which fibers 1 are formed. In particular, when a silicon substrate is used as a raw material, on the surface of a joined portion between the substrate and fibers 1 in a formation process of fibers 1, fibers 1 are aggregated densely, so that fibers 1 may be easily melted and thus connection portion 6 is easily formed.

Note here that as the gas required to form fiber 1, in addition to oxygen, a gas having an oxidation effect (that is to say, a gas that supplies oxygen) such as dinitrogen monoxide ($N_2O$) and carbon monoxide (CO) can be used.

However, since such gases contain impurities other than oxygen, and affect the formation process of fibers 1 and sheet-like fiber structure 20, it is necessary to appropriately control the concentration, temperature and pressure.

Note here that a deposition state varies depending upon conditions such as the size of fiber 1, a pressure of the atmosphere at the time of formation of fibers 1, an oxygen concentration of the atmosphere, and a temperature of the atmosphere. Therefore, by changing such conditions, fiber 1 having a desirable shape and sheet-like fiber structure 20 can be formed. The diameter (thickness) of fiber 1 can be varied in a range of not less than 0.01 µm and not more than 1 µm. The length of fiber 1 can be varied in a range of not less than 1 µm and not more than 500 µm.

In a region of the thus formed sheet-like fiber structure 20 in which a plurality of fibers 1 are formed, the surface area of amorphous silicon dioxide becomes extremely large. On the other hand, many void portions 2 are present in the vicinity of amorphous silicon dioxide. Sheet-like fiber structure 20 includes fibers 1 made of amorphous silicon dioxide and void portion 2. A large amount of liquid materials such as electrolytic solution 3 can be contained in void portion 2.

Figure 5:
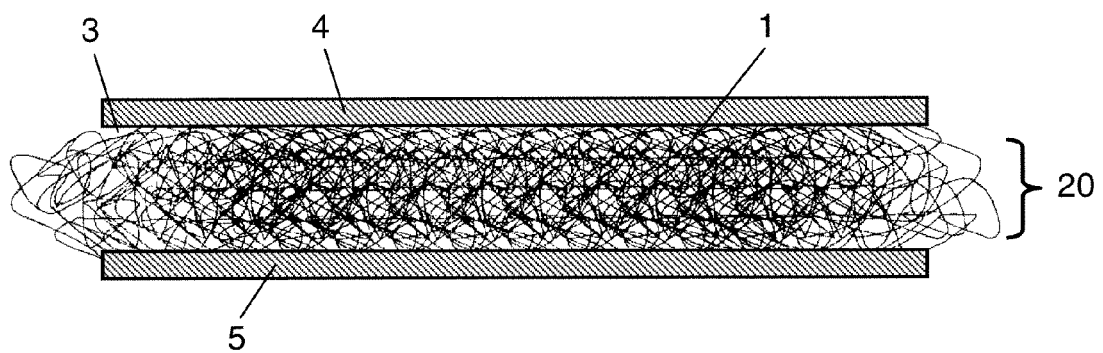
FIG. 5 is a conceptual view of a battery using the sheet-like fiber structure in accordance with the first exemplary embodiment of the present invention.

FIG. 5 is a conceptual view of a battery using sheet-like fiber structure 20 in accordance with the first exemplary embodiment of the present invention. Electrodes 4 and 5 made of different materials such as aluminum and cobalt are disposed on both sides of sheet-like fiber structure 20 including void portions 2 filled with electrolytic solution 3. When the ionization tendency is different between electrodes 4 and 5, ions in electrolytic solution 3 move between the electrodes. Thus, it is possible to produce a battery from which an electric current is taken out.

The distance between electrode 4 and electrode 5 is a factor for determining the moving time of ions. In order to reduce the internal resistance of a battery, a distance between the electrodes is preferably as small as possible. However, when the distance between the electrodes is made to be small, short circuit easily occurs between electrode 4 and electrode 5. In general, a separator to be used in a battery is used for preventing short circuit, but the separator should not inhibit flow of ions. Therefore, paper, polymer fiber, and the like, having voids inside are used, and an electrolytic solution is contained in the voids.

Sheet-like fiber structure 20 formed of fibers 1 is excellent as a separator. When electrolytic solution 3 is allowed to be contained inside, since portions other than fibers 1 are void portions 2, an extremely large amount of electrolytic solution 3 can be allowed to be contained. Therefore, the flow of ions is not prevented. Furthermore, since a diameter of fiber 1 is not less than 0.01 µm and not more than 1 µm, which is smaller than that of a conventional fiber, a large amount of electrolytic solution can be allowed to be contained or to pass (liquid permeability). Furthermore, the length of fiber 1 can be made to be not less than 1 µm and not more than 500 µm, and the maximum interval between fiber 1 and its neighboring fiber 1 can be made to be not less than 1 µm and not more than 50 µm. Therefore, while an effect of preventing short circuit between the electrodes is maintained, the content amount of the electrolytic solution can be increased as much as possible. The values of the diameter, length, and maximum interval of fiber 1 are determined depending upon the degree of hydrophilic property or water holding capacity desired to be provided.

Sheet-like fiber structure 20 can be used even at high temperatures and high oxygen concentration. Since neighboring fibers 1 are melted by heat and formed in a mesh structure, the strength can be improved and characteristics that are not possessed by a carbon-based fiber can be achieved.

In this exemplary embodiment, connection portion 6 is formed by thermal melting, but connection portion 6 may be formed by resin that has been filled. Furthermore, resin may be filled and connection portion 6 may be formed by thermal melting. By filling resin in void portions 2, the connection strength of sheet-like fiber structure 20 can be increased. Note here that as the resin, for example, an adhesive agent can be used.

Second Exemplary Embodiment

Figure 6:
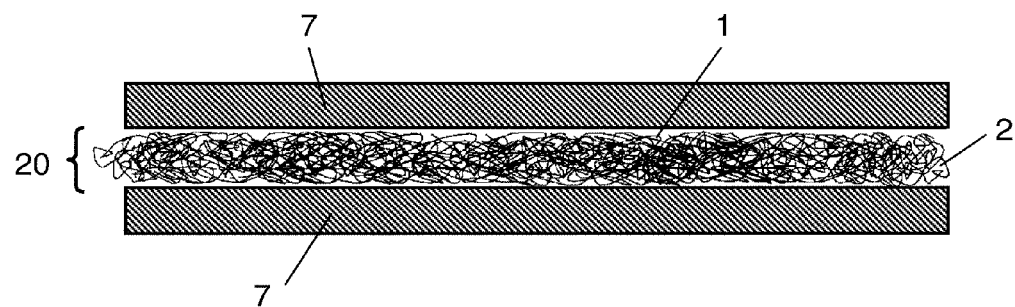
FIG. 6 is a conceptual view of a heat insulation material using a sheet-like fiber structure in accordance with a second exemplary embodiment of the present invention.

FIG. 6 is a conceptual view of a heat insulation material using sheet-like fiber structure 20 in accordance with a second exemplary embodiment of the present invention. A method for producing sheet-like fiber structure 20 is the same as that in the first exemplary embodiment. Fibers 1 having void portions 2 are sandwiched between substrates 7. For example, substrate 7 includes at least one of plane-shaped glass, silicon, quartz, ceramic, resin, and metal. Since sheet-like fiber structure 20 includes many void portions 2, heat insulation between substrates 7 is achieved.

Figure 7:
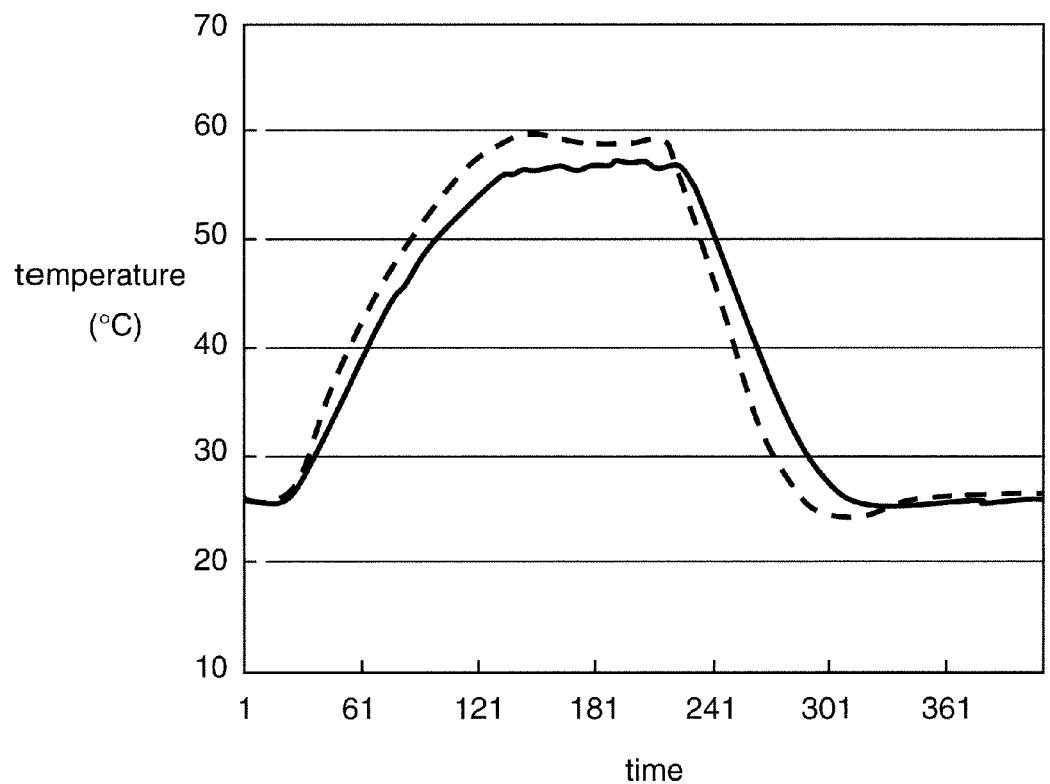
FIG. 7 is a graph showing properties of the sheet-like fiber structure in accordance with the second exemplary embodiment of the present invention.

FIG. 7 is a graph showing properties of sheet-like fiber structure 20 in accordance with the second exemplary embodiment of the present invention. FIG. 7 shows a state in which fibers 1 are sandwiched between two glass substrates as substrate 7, and heat is conducted between the glass substrates. The graph shows a change over time of a temperature of another substrate 7 when heat is applied from one substrate 7. A case in which nothing is sandwiched between substrates 7 is shown by a broken line, and a case in which fibers 1 are sandwiched between substrates 7 is shown by a solid line. When fibers 1 are sandwiched, heat conductivity is reduced as compared with the case in which nothing is sandwiched.

Furthermore, when void portion 2 is made to be vacuum, heat conduction effect is further increased. When sheet-like fiber structure 20 is not provided, when the inside of substrates 7 is made to be vacuum, substrates 7 are adhesively attached to each other by a pressure applied from the outside. However, when sheet-like fiber structure 20 is provided, substrates 7 are not brought into contact with each other. Furthermore, sheet-like fiber structure 20 is brought into contact with substrates 7, but since fiber 1 of sheet-like fiber structure 20 has a diameter of not more than 1 µm, and a length of not less than 1 µm. Thus, the aspect ratio is high. Thereby, the heat conductivity becomes smaller as compared with conventional one. Note here that fibers 1 having void portions 2 may be entirely formed between substrates 7, and may be patterned and formed only at specified portions.

Third Exemplary Embodiment

Figure 8:
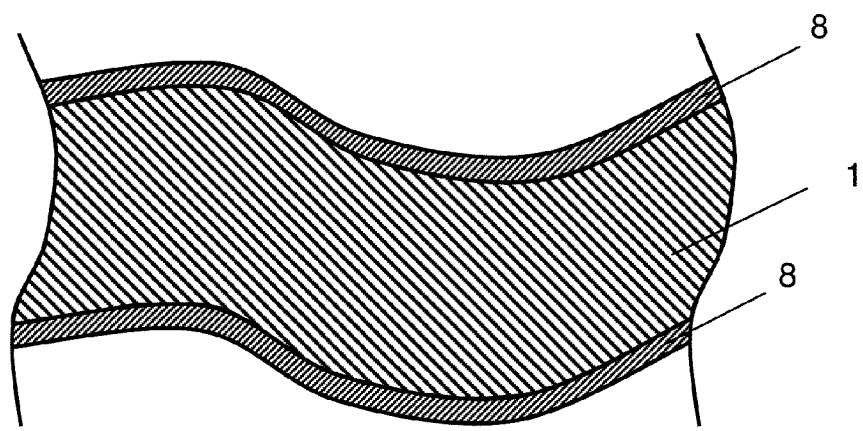
FIG. 8 is an enlarged sectional view of a sheet-like fiber structure that is surface-modified with a water-repellent film in accordance with a third exemplary embodiment of the present invention.

FIG. 8 is an enlarged sectional view of a sheet-like fiber structure that has been surface-modified with a water-repellent film in accordance with a third exemplary embodiment of the present invention. In this exemplary embodiment, the surface of fiber 1 of sheet-like fiber structure 20 produced by the same method as in the first exemplary embodiment is modified with water-repellent film 8. Water-repellent film 8 can be formed by, for example, a polymer to which a $CF_2$ chain links, a fluorine compound containing a CF group, an alkylsilyl group, a fluorosilyl group, and a long chain alkyl group. When the surface of fiber 1 is modified with a chemical substance having a water repellent effect, water-repellent film 8 is formed on the surface of fiber 1. As a result, sheet-like fiber structure 20 exhibits an extremely high water repellent property, water in a liquid state, for example, a water droplet cannot enter the inside of a sheet. On the other hand, water in an air state, for example, water vapor can pass through the sheet. Moreover, since sheet-like fiber structure 20 has high void percentage, air can pass through sheet-like fiber structure 20 easily. That is to say, since sheet-like fiber structure 20 can be used as a film that allows water vapor to pass but does not allow water to pass. This film is used for a waterproof sheet, waterproof cloth, and the like, which have high breathability (air permeability).

Note here that fibers 1 that have been surface-modified with water-repellent film 8 can be used in a state in which they are sandwiched by substrates 7 as shown in FIG. 6. When sheet-like fiber structure 20 is sandwiched by substrates 7, sheet-like fiber structure 20 can maintain the strength as a film. Note here that when substrate 7 includes a plurality of holes, water vapor can pass through the holes in substrate 7, and, therefore, it is useful for a waterproof sheet, and the like.

Fourth Exemplary Embodiment

Figure 9:
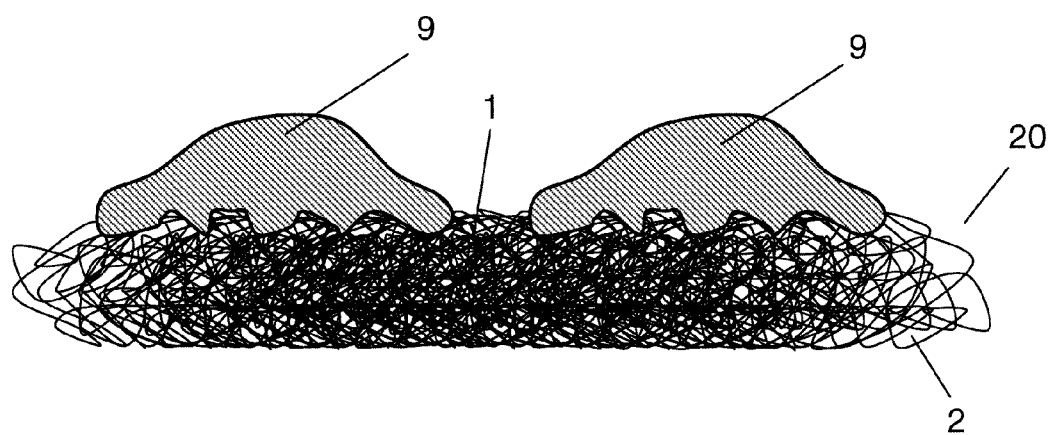
FIG. 9 is a conceptual view showing a case in which a sheet-like fiber structure is used in cell culture in accordance with a fourth exemplary embodiment of the present invention.

In this exemplary embodiment, sheet-like fiber structure 20 produced by the same method as in the first exemplary embodiment is used as a scaffold for a culture dish to be used for culturing adhesive cells. FIG. 9 is a conceptual view showing a case in which sheet-like fiber structure 20 is used in cell culture.

Cells 9 are seeded on the upper surface of sheet-like fiber structure 20 such that they adhere to the surface. Thus, cells 9 adhere and extend on sheet-like fiber structure 20, and thus, cell culture can be carried out. Herein, sheet-like fiber structure 20 is the same as that produced in the first exemplary embodiment, and it includes fibers 1 made of amorphous silicon dioxide, which are intertwined with each other, thereby forming void portions 2. Furthermore, as cell 9 to be cultured, an adhesive cell is suitable.

With the above-mentioned configuration, cells 9 can be cultured in a state that is nearer to the inside of a living body. That is to say, since void portions 2 are included, not only exchanging culture solutions, but also supplying nutrient to cells 9 that are being cultured can be carried out easily. Furthermore, waste matters exhausted from cells 9 move to the lower surface of sheet-like fiber structure 20 via void portion 2, and easily exhausted by sheet-like fiber structure 20. Therefore, waste matters do not accumulate in the vicinity of cells 9 that are being cultured. As a result, cells 9 can be cultured for a long time, and thus the survival rate of cells 9 can be improved.

Note here that when a scaffold is formed of a polymer material as in a conventional one, there are problems of heat resistance and chemical resistance. However, since sheet-like fiber structure 20 in this exemplary embodiment includes an inorganic material made of $SiO_2$, it is excellent in heat resistance and chemical resistance. Sheet-like fiber structure 20 has heat resistance temperature of not lower than 1000° C., and surface treatment by heat treatment can be carried out easily. As the chemical resistance, sheet-like fiber structure 20 is not affected by substances other than hydrofluoric acid, and is strong with respect to an alkaline solution. In this way, it is possible to provide a scaffold having high percentage of voids per unit area and excellent heat resistance and chemical resistance.

Fifth Exemplary Embodiment

Figure 10:
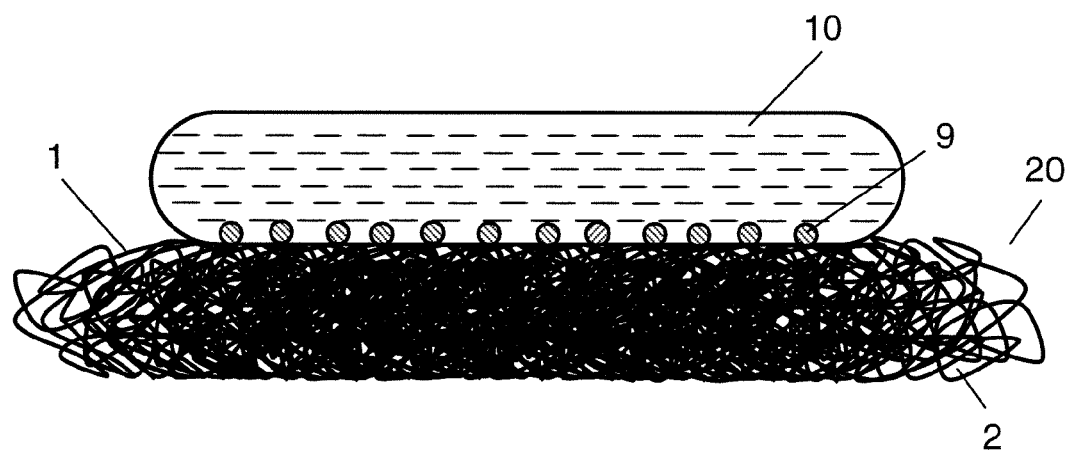
FIG. 10 is a conceptual view showing a case in which a sheet-like fiber structure is used in cell culture in accordance with a fifth exemplary embodiment of the present invention.

In this exemplary embodiment, the surface of fibers 1 of sheet-like fiber structure 20 produced by the same method as in the first exemplary embodiment is surface-modified with water-repellent film 8. Sheet-like fiber structure 20 is used as a scaffold of a culture dish to be used for culturing adhesive cells. FIG. 10 is a conceptual view showing a case in which sheet-like fiber structure 20 is used in cell culture.

By dropping solution 10 such as a culture solution to the upper surface of sheet-like fiber structure 20, cells 9 are seeded in solution 10. Thus, cells 9 are cultured in solution 10. Herein, sheet-like fiber structure 20 is the same as that produced in the third exemplary embodiment, and the surface of fiber 1 is surface-modified with water-repellent film 8. Furthermore, fibers 1 made of amorphous silicon dioxide are intertwined with each other, thereby forming void portions 2.

With the above-mentioned configuration, even when cells 9 are cultured in solution 10 on sheet-like fiber structure 20, solution 10 can be present stably on the surface of sheet-like fiber structure 20 by water-repellent film 8. Therefore, stable cell culture can be carried out.

Furthermore, sheet-like fiber structure 20 in which water-repellent film 8 is formed on the surface of fiber 1 can appropriately supply gas to solution 10 in the vicinity of cells 9. When it is used as a scaffold for a culture dish to be used for culturing cells, pH of the solution (culture solution) is required to be kept acidic. Therefore, in general, carbon dioxide or carbon dioxide gas is added to atmosphere at about 5% and allowed to be solved in a solution, thereby controlling the acidity. However, carbon dioxide can be melted only from a portion in which a solution as a liquid phase and atmosphere as a vapor phase are brought into contact with each other. Therefore, in a region of the solution (culture solution) that is located distant from the vapor phase, the acidity cannot be controlled precisely. As in sheet-like fiber structure 20 in this exemplary embodiment, when a scaffold having air permeability is applied for a cell culture dish, gas can be supplied to the vicinity in which cells 9 in solution 10 are attached and extended, which is a region in which carbon dioxide is not easily melted conventionally. As a result, cells 9 can be efficiently cultured.

Furthermore, as in this exemplary embodiment, when water-repellent film 8 is formed on the surface, solution 10 such as a culture solution does not penetrates into the inside of sheet-like fiber structure 20. Thus, the inside, that is, void portion 2 is in a vapor phase state. Therefore, even when cells 9 are attached to the surface of sheet-like fiber structure 20, carbon dioxide is appropriately supplied to the vicinity of cells 9, so that the acidity of solution 10 can be kept appropriately.

Note here that examples of gas to be supplied include nitrogen, oxygen, and the like, if necessary, in addition to carbon dioxide. The types of gases are not necessarily limited.

Sixth Embodiment

Figure 11:
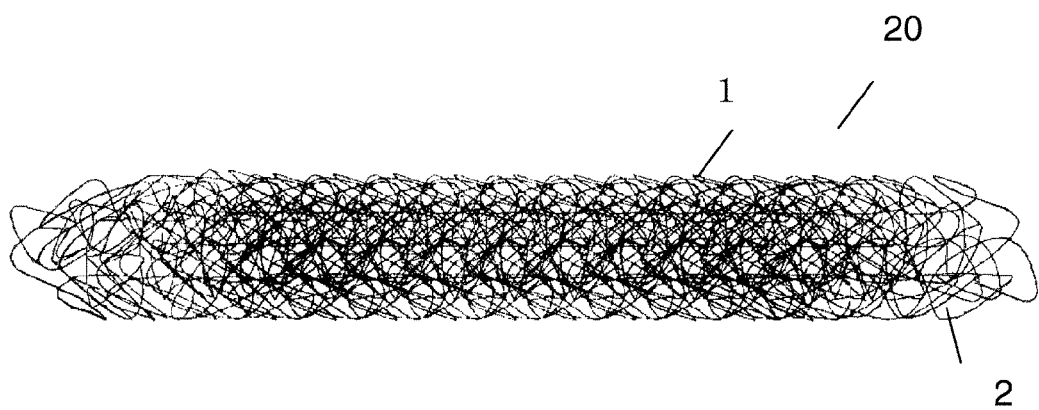
FIG. 11 is a conceptual view showing a case in which a sheet-like fiber structure is used for a holding material in accordance with a sixth embodiment of the present invention.

In this embodiment, sheet-like fiber structure 20 produced by the same method as in the first embodiment is used as a holding material for biomolecules such as protein. FIG. 11 is a conceptual view showing a case in which sheet-like fiber structure 20 is used for a holding material.

For example, a solution containing a biomolecule is dropped to sheet-like fiber structure 20, so that the biomolecule is allowed to adhere on a fiber surface. Thus, the biomolecule is held by sheet-like fiber structure 20. Herein, sheet-like fiber structure 20 is the same as that produced in the first embodiment and has void portions 2 provided by fibers 1 made of amorphous silicon dioxide which are intertwined with each other.

The biomolecule is placed on sheet-like fiber structure 20, and irradiated with laser from the upper side. Thereby, the biomolecule is ionized. By ionizing the biomolecule, for example, a mass of the biomolecule can be analyzed.

Conventionally, when a biomolecule is ionized, the biomolecule is expanded two-dimensionally on the surface of the substrate. However, in this embodiment, since sheet-like fiber structure 20 has void portions 2, the biomolecule is held three-dimensionally in a wider range as compared with conventionally. Therefore, even when a range which is irradiated with laser is the same as conventionally, an amount of a biomolecule irradiated with laser is increased. As a result, an ionized amount of a biomolecule by laser irradiation can be increased.

Thus, since the biomolecule is concentrated and confined in a predetermined range, ionization can be carried out even with a small amount of specimens.

INDUSTRIAL APPLICABILITY

As mentioned above, a sheet-like fiber structure of the present invention has not only liquid permeability and voltage resistance, but also high heat resistance and chemical resistance. Accordingly, it can be used for a separator for preventing short circuit between electrodes or a scaffold for cell culture.

REFERENCE MARKS IN DRAWINGS 1 fiber
2 void portion
3 electrolytic solution
4 electrode
5 electrode
6 connection portion
7 substrate
8 water-repellent film
9 cell
10 solution

The invention claimed is:
1. A sheet-like fiber structure comprising:
a silicon substrate,
a plurality of fibers made of amorphous silicon dioxide, each of the plurality of fibers includes a metal selected from the group consisting of Pt, Fe, Co, Ni and Au as a core,
wherein each of the plurality of fibers is curled,
the plurality of fibers are disposed on a surface of the silicon substrate,
a plurality of the plurality of fibers have bifurcation areas, in which one fiber bifurcates into two fibers at the bifurcation area,
the plurality of fibers are intertwined with each other and connected to each other, for forming void portions,
a part of each of the plurality of fibers is melted, so that the melted part of one given fiber is bonded to the melted part of another given fiber so as to form a connection portion, and
the density of fibers of the plurality of fibers and the density of connection portions are both greater adjacent the surface of the silicon substrate relative to other portions of the plurality of fibers.

2. The sheet-like fiber structure of claim 1, wherein a length of each given fiber of the plurality of fibers is not less than 1 μm and not more than 500 μm.

3. The sheet-like fiber structure of claim 1, wherein a maximum interval between one given fiber of the plurality of fibers and another given fiber of the plurality of fibers next to the one given fiber is not less than 1 μm and not more than 50 μm.

4. The sheet-like fiber structure of claim 1, wherein a thickness of each given fiber of the plurality of fibers is not less than 0.01 μm and not more than 1 μm.

5. A battery comprising:
the sheet-like fiber structure of claim 1; and
electrodes sandwiching the sheet-like fiber structure,
wherein the void portions are filled with electrolytic solution.

6. A heat insulation material comprising:
the sheet-like fiber structure of claim 1; and
substrates sandwiching the sheet-like fiber structure.

7. The heat insulation material of claim 6, wherein the substrates comprise at least one of glass, silicon, quartz, ceramic, resin, and metal.

8. The heat insulation material of claim 6, wherein the void portions are vacuum.

9. The heat insulation material of claim 6, wherein the fibers are formed only at a specified portion between the substrates.

10. A waterproof sheet comprising:
the sheet-like fiber structure of claim 1,
wherein a surface of each given fiber of the plurality of fibers is surface-modified with a water-repellent film.

11. The waterproof sheet of claim 10, further comprising substrates sandwiching the sheet-like fiber structure,
wherein each of the substrates includes a plurality of holes.

12. A scaffold for cell culture, comprising the sheet-like fiber structure of claim 1.

13. The scaffold for cell culture of claim 12, wherein a surface of each given fiber of the plurality of fibers is surface-modified with a water-repellent film.

14. A holding material comprising the sheet-like fiber structure of claim 1.

15. A sheet-like fiber structure comprising:
a silicon substrate,
a plurality of fibers made of amorphous silicon dioxide, each of the plurality of fibers includes a metal as a core,
wherein each of the plurality of fibers is curled,
the plurality of fibers are disposed on a surface of the silicon substrate,
a plurality of the plurality of fibers have bifurcation area, in which one fiber bifurcates into two fibers at the bifurcation area,
the plurality of fibers are intertwined with each other and connected to each other, for forming void portions,
a part of each of the plurality of fibers is melted, so that the melted part of one given fiber is bonded to the melted part of another given fiber so as to form a connection portion, and
the density of fibers of the plurality of fibers and the density of connection portions are both greater adjacent the surface of the silicon substrate relative to other portions of the plurality of fibers.

16. The sheet-like fiber structure according to claim 15, wherein the metal is selected from the group consisting of Pt, Fe, Co, Ni and Au.

17. The sheet-like fiber structure of claim 1, wherein
the one given fiber and the another given fiber are bonded together without utilizing a binding agent,
a melted bonding portion is formed between the one given fiber and the another given fiber,
the melted bonding portion is made of the same material of the plurality of fibers, and
a length of the melted bonding portion in a direction perpendicular to a long direction of the one given fiber is larger than a diameter distance of the one given fiber.

18. The sheet-like fiber structure according to claim 15, wherein
the one given fiber and the another given fiber are bonded together without utilizing a binding agent,
a melted bonding portion is formed between the one given fiber and the another given fiber,
the melted bonding portion is made of the same material of the plurality of fibers, and
a length of the melted bonding portion in a direction perpendicular to a long direction of the one given fiber is larger than a diameter distance of the one given fiber.

19. A sheet-like fiber structure comprising:
a first surface,
a second surface,
a plurality of fibers disposed between the first surface and the second surface, made of amorphous silicon dioxide, each of the plurality of fibers includes a metal selected from the group consisting of Pt, Fe, Co, Ni and Au as a core,
wherein the first surface is formed as a surface of a joined portion between a silicon substrate and the fibers when the silicon substrate is used as a raw material,
each of the plurality of fibers is curled,
the plurality of fibers have bifurcation areas, in which one fiber bifurcates into two fibers at the bifurcation area,
the plurality of fibers are intertwined with each other and connected to each other, for forming void portions,
a part of each of the plurality of fibers is melted, so that the melted part of one given fiber is bonded to the melted part of another given fiber so as to form a connection portion, and
the density of fibers of the plurality of fibers and the density of connection portions are both greater adjacent the first surface relative to other portions of the plurality of fibers.

20. A sheet-like fiber structure comprising:
a first surface,
a second surface,
a plurality of fibers disposed between the first surface and the second surface, made of amorphous silicon dioxide, each of the plurality of fibers includes a metal as a core,
wherein the first surface is formed as a surface of a joined portion between a silicon substrate and the fibers when the silicon substrate is used as a raw material,
each of the plurality of fibers is curled,
the plurality of fibers have bifurcation area, in which one fiber bifurcates into two fibers at the bifurcation area,
the plurality of fibers are intertwined with each other and connected to each other, for forming void portions,
a part of each of the plurality of fibers is melted, so that the melted part of one given fiber is bonded to the melted part of another given fiber so as to form a connection portion, and
the density of fibers of the plurality of fibers and the density of connection portions are both greater adjacent the first surface relative to other portions of the plurality of fibers.

* * * * *